United States Patent [19]

Connor et al.

[11] Patent Number: 5,916,914
[45] Date of Patent: Jun. 29, 1999

[54] COMPOUNDS AND METHOD OF TREATING PSYCHOSIS AND SCHIZOPHRENIA

[75] Inventors: David Thomas Connor; Stephen Joseph Johnson; Suzanne Ross Kesten; Steven Robert Miller; Paul Charles Unangst; Lawrence David Wise, all of Ann Arbor, Mich.

[73] Assignee: Warner-Lambert Company, Morris Plains, N.J.

[21] Appl. No.: 08/907,680

[22] Filed: Aug. 8, 1997

[51] Int. Cl.$^6$ .................. A61K 31/35; C07D 311/02; C07D 319/12
[52] U.S. Cl. ..................... 514/456; 549/283; 549/378
[58] Field of Search .................. 549/283, 378; 514/456

[56] References Cited

U.S. PATENT DOCUMENTS

| | | | |
|---|---|---|---|
| 2,547,365 | 4/1951 | Bock et al. | 260/567.6 |
| 2,599,001 | 6/1952 | Kerwin et al. | 260/570.7 |
| 3,154,581 | 10/1964 | Dice | 260/570.7 |
| 3,159,676 | 12/1964 | Spickett et al. | 260/564 |
| 3,192,253 | 6/1965 | Boscott et al. | 260/501 |
| 3,663,712 | 5/1972 | Schmelling et al. | 424/330 |
| 4,010,280 | 3/1977 | Maruyama et al. | 424/316 |
| 5,760,050 | 6/1998 | Connor et al. | 514/291 |

OTHER PUBLICATIONS

J. Augstein, et al., *J Med Chem*, "Some Cardiovascular Effects of a Series of Aryloxyalkylamines," 1965, 8, 356.

L.H. Smith, et al, *J Med Chem*, "β–Adrenergic Blocking Agents. 17. 1–Phenoxy–3–phenoxyalkylamino–2–propanols and 1–Alkoxyalkylamino–3–phenoxy–2–propanols," 1977, 20:12, 1653–1656.

*Primary Examiner*—Johann Richter
*Assistant Examiner*—Joseph Murray
*Attorney, Agent, or Firm*—Todd M. Crissey

[57] ABSTRACT

This invention relates to compounds that are antagonists of dopamine D4 receptors, and to methods of treating psychosis and schizophrenia using a compound that is an antagonist of dopamine D4 receptors.

16 Claims, No Drawings

COMPOUNDS AND METHOD OF TREATING PSYCHOSIS AND SCHIZOPHRENIA

FIELD OF THE INVENTION

This invention relates to compounds that are antagonists of dopamine D4 receptors and to methods of treating psychosis and schizophrenia using a compound that is an antagonist of dopamine D4 receptors.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are called dopamine receptor antagonists. It is also well-known that dopamine receptor antagonists are useful in the treatment of schizophrenia and psychosis.

Recently, it has been discovered that more than one type of dopamine receptor exists, and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. For example, D2 receptors are found in high concentrations in the frontal cortex and limbic region, which are associated with cognitive and emotional function and also in striatal regions which are associated with motor activity.

D2 subtype receptor antagonists have been used to treat psychosis and schizophrenia, but have undesirable extrapyramidal side effects and produce tardive dyskinesia which is thought to be due to their striatal effects. In contrast, D4 receptors are found in highest concentrations in the frontal cortex and limbic regions. Therefore, D4 receptor antagonists can produce antipsychotic efficacy and lack the extra pyramidal side effects and tardive dyskinesias. Moreover, it has been observed that the levels of dopamine D4 receptors are elevated in schizophrenics.

Thus, it would be useful to have compounds that are selective D4 antagonists for the treatment of psychosis and schizophrenia.

SUMMARY OF THE INVENTION

The present invention provides compounds having the Formula I

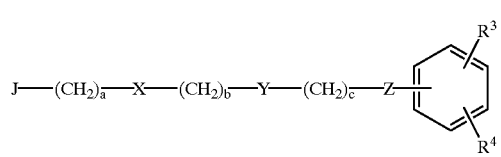

wherein J is

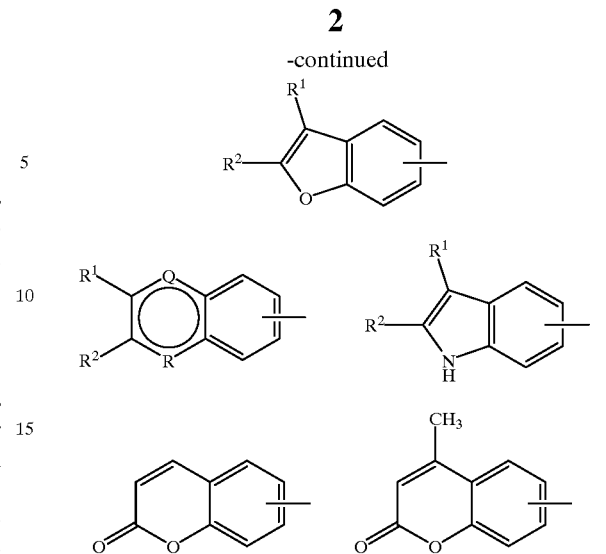

R is O or N;

Q is a bond, CH, or CCH$_3$;

X is O, S, or NH;

Y is NH or a bond;

Z is O, S, NH, or a bond;

a, b, and c are independently 0 to 3;

$R^1$ is hydrogen or $R^1$ and $R^2$ taken together form a benzene ring;

$R^2$ is hydrogen; and $R^3$ and $R^4$ are independently hydrogen, hydroxyl, $C_1$–$C_6$ alkyl, $C_1$–$C_6$ alkoxy, halogen, nitro, phenyl, cyano, carboxy, carboxamido, carboalkoxy or hydroxymethyl, and the pharmaceutically acceptable salts, esters, amides, and prodrugs thereof.

In a particular embodiment of the compounds of Formula I, J is

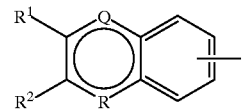

In another particular embodiment, J is

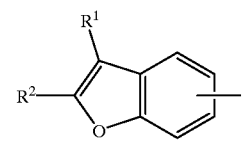

In another particular embodiment, J is

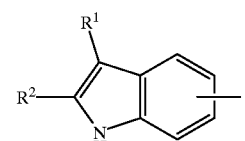

In another particular embodiment, J is

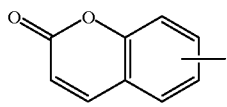

In another particular embodiment, J is

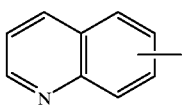

In another particular embodiment, J is

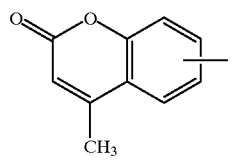

In a preferred embodiment, a is 0, b is 2, c is 3, X is O, Y is NH, and Z is O.

In another preferred embodiment, a is 1, X is NH, b is 2, and Y is NH, c is 0, and Z is a bond.

In another preferred embodiment, a is 1, X is NH, b is 2, Y is O, c is 0, and Z is a bond.

In another preferred embodiment, $R^3$ and $R^4$ are independently hydrogen, $C_1$–$C_6$ alkyl, halogen, or hydroxymethyl.

In another preferred embodiment, $R^3$ and $R^4$ are hydrogen.

In a preferred embodiment, the compound of Formula I is a hydrohalide salt.

In a more preferred embodiment, the hydrohalide salt is the hydrochloride salt.

In another preferred embodiment, a compound of Formula I has the structure

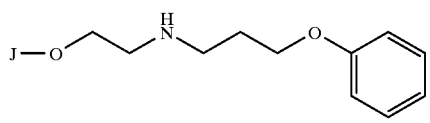

In another preferred embodiment, a compound of Formula I has the structure

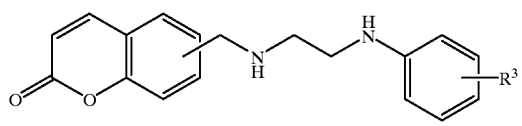

Also provided by the present invention is a pharmaceutically acceptable composition that comprises a compound of Formula I.

Also provided by the present invention is a method of treating psychosis, the method comprising administering to a patient having psychosis a therapeutically effective amount of a compound of Formula I.

Also provided by the present invention is a method of treating schizophrenia, the method comprising administering to a patient having schizophrenia a therapeutically effective amount of a compound of Formula I.

Also provided by the present invention are the compounds

6-[2-(3-Phenoxy-propylamino)-ethoxy]-chromen-2-one hydrochloride;
(3-Phenoxy-propyl)-[2-quinolin-6-yloxy)-ethyl]-amine hydrochloride;
8-[2-(3-Phenoxy-propylamino)-ethoxy]-chromen-2-one hydrochloride;
7-[2-(3-Phenoxy-propylamino)-ethoxy]-chromen-2-one hydrochloride;
[2-(Dibenzofuran-2-yloxy)-ethyl]-(3-phenoxypropyl)-amine hydrochloride;
4-Methyl-7-[2-(3-phenoxy-propylamino)-ethoxy]-chromen-2-one hydrochloride;
4-Methyl-6-[2-(3-phenoxy-propylamino)-ethoxy]-chromen-2-one hydrochloride;
[2-(Benzofuran-5-yloxy)-ethyl]-(3-phenoxy-propyl)-amine hydrochloride;
7-[(2-Phenylamino-ethylamino)-methyl]-chromen-2-one;
7-{[2-(3-Chloro-4-hydroxymethyl-phenylamino)-ethylamino]-methyl}-chromen-2-one;
7-{[2-(3,4-Dimethyl-phenylamino)-ethylamino]-methyl}-chromen-2-one;
7-[(2-p-Tolylamino-ethylamino)-methyl]-chromen-2-one;
7-{[2-(3-Chloro-phenylamino)-ethylamino]-methyl}-chromen-2-one dihydrochloride;
7-{[2-(4-Chloro-phenylamino)-ethylamino]-methyl}-chromen-2-one;
7-{[2-(3-Chloro-4-methyl-phenylamino)-ethylamino]-methyl}-chromen-2-one;
6-[(2-Phenylamino-ethylamino)-methyl]-chromen-2-one;
6-{[2-(3-Chloro-4-methyl-phenylamino)-ethylamino]-methyl}-chromen-2-one hydrochloride;
7-[(3-Phenylamino-propylamino)-methyl]-chromen-2-one;
6-[(2-Phenoxy-ethylamino)-methyl]-chromen-2-one hydrochloride;
6-[(2-p-Tolyloxy-ethylamino)-methyl]-chromen-2-one;
6-{[2-(4-Chloro-phenoxy)-ethylamino]-methyl}-chromen-2-one;
7-[(2-Phenoxy-ethylamino)-methyl]-chromen-2-one;
7-[(2-p-Tolyloxy-ethylamino)-methyl]-chromen-2-one;
7-{[2-(4-Chloro-phenoxy)-ethylamino]-methyl}-chromen-2-one;
7-[(2-Phenylsulfanyl-ethylamino)-methyl]-chromen-2-one hydrochloride;
7-[(3-Phenyl-propylamino)-methyl]-chromen-2-one;
7-{[3-(4-Chloro-phenoxy)-propylamino]-methyl}-chromen-2-one;
7-[(3-p-Tolyloxy-propylamino)-methyl]-chromen-2-one; or
6-[(3-Phenoxy-propylamino)-methyl]-chromen-2-one.

DETAILED DESCRIPTION OF THE INVENTION

The present invention provides compounds having the Formula I

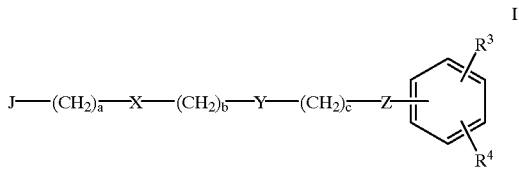

wherein

J is

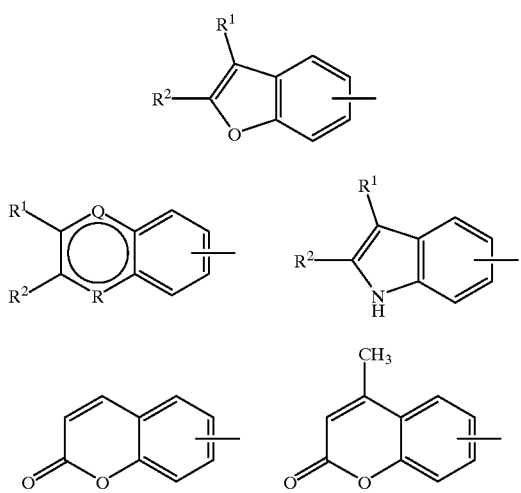

R is O or N;
Q is a bond, CH, or CCH$_3$;
X is O, S, or NH;
Y is NH or a bond;
Z is O, S, NH, or a bond;
a, b, and c are independently 0 to 3;
R$^1$ is hydrogen or R$^1$ and R$^2$ taken together form a benzene ring;
R$^2$ is hydrogen; and
R$^3$ and R$^4$ are independently hydrogen, hydroxyl, C$_1$–C$_6$ alkyl, C$_1$–C$_6$ alkoxy, halogen, nitro, phenyl, cyano, carboxy, carboxamido, carboalkoxy or hydroxymethyl, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "carboxy" means a carboxylic acid functional group, i.e., —CO$_2$H.

The term "carboalkoxy" means an alkyl ester of a carboxylic acid functional group, i.e., —CO$_2$alkyl. A preferred carboxyalkyloxy group is carboxymethoxy.

The term "carboxamido" means a —CONH$_2$ group. It is noted that the two hydrogens on the nitrogen atom may be substituted with substituents that are well-known to those skilled in the art, such as alkyl groups.

The symbol "—" means a bond.

The term "patient" means humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, nontoxic esters of the compounds of this invention include C$_1$–C$_6$ alkyl esters wherein the alkyl group is a straight or branched chain. Acceptable esters also include C$_5$–C$_7$ cycloalkyl esters as well as arylalkyl esters such as, but not limited to benzyl. C$_1$–C$_4$ alkyl esters are preferred. Esters of the compounds of the present invention may be prepared according to conventional methods.

Examples of pharmaceutically acceptable, nontoxic amides of the compounds of this invention include amides derived from ammonia, primary C$_1$–C$_6$ alkyl amines and secondary C$_1$–C$_6$ dialkyl amines wherein the alkyl groups are straight or branched chain. In the case of secondary amines, the amine may also be in the form of a 5- or 6-membered heterocycle containing one nitrogen atom. Amides derived from ammonia, C$_1$–C$_3$ alkyl primary amines and C$_1$–C$_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art.

The compositions can be administered to humans and animals either orally, rectally, parenterally (intravenously, intramuscularly, or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferred. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof, including racemic mixtures, form part of this invention.

The following examples are intended to illustrate particular embodiments of the invention and are not intended to limit the scope of the disclosure or the claims in any manner.

EXAMPLES

The compounds of the present invention are prepared by the following methods, as illustrated in Schemes I and II.

Scheme I

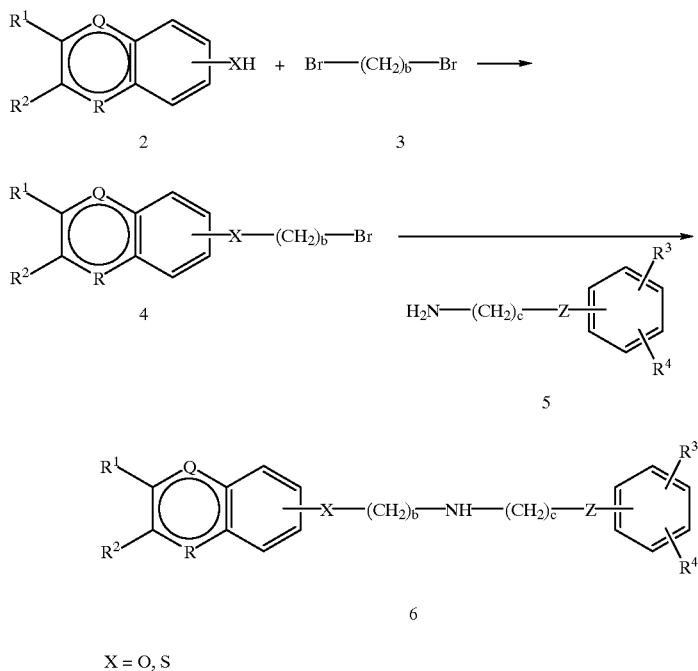

X = O, S

Scheme II

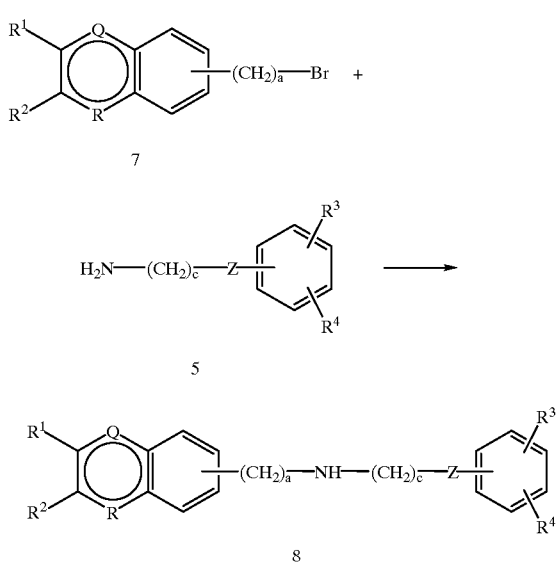

Substituted heterocyclic phenols or thiophenols (2) are combined with dibromoalkanes (3) in acetone or 2-butanone at 50° C. to 80° C. for 8 to 48 hours in the presence of a base such as potassium carbonate or sodium carbonate to yield intermediate bromoalkyl ethers (4) (Scheme I). The reaction may also be performed in water at 50° C. to 100° C. with sodium hydroxide or potassium hydroxide as the base, in an alcohol solvent such as methanol or ethanol with sodium methoxide or sodium ethoxide as the base, or in a mixed water/organic solvent system under phase transfer conditions.

The bromoalkyl ethers (4) are reacted with substituted amines (5) in a solvent such as benzene, toluene, xylene, ethanol, acetonitrile, or N,N-dimethylformamide at 70° C. to 140° C. for 8 to 48 hours to yield the products (6). An additional molar equivalent of the amine (5) may be included in the reaction mixture in order to trap liberated hydrogen bromide, or an additional base such as sodium carbonate or potassium carbonate may be included for this purpose. Similarly, substituted alkyl bromides (7) (Scheme II) are reacted with substituted amines (5) to yield the products (8) under the reaction conditions used for the reaction of 4 with 5.

As starting materials, 2 and 7 are known or may be readily prepared by known methods. For the preparation of 2, see T. Harayama, et al., *Heterocycles*, 1994;39:613, and for the preparation of 7, see K. M. Jainamma and S. Sethna, *J. Indian Chem. Soc.*, 1973;50:790. Similarly, 5 are known or may be readily prepared by known methods, such as J. Augstein, et al., *J. Med. Chem.*, 1965;8:356 and G. S. Poindexter, *Synthesis*, 1981:541.

Example 1

6-(2-Bromo-ethoxy)-chromen-2-one

A mixture of 6-hydroxy-chromene-2-one, which can be synthesized in accordance with the procedure set forth by T. Harayama, K. Katsuno, H. Nishioka, M. Fujii, Y. Nishita, H. Ishii, and Y. Kaneko, *Heterocycles*, 1994;39:613, (3.2 g, 19.7 mmol), 1,2-dibromoethane (6.7 mL, 14.6 g, 78 mmol), and potassium carbonate (5.4 g, 39 mmol) in 150 mL of acetone is stirred at reflux for 48 hours. The cooled reaction mixture is added to 1.0 L of water and 250 mL of ethyl acetate. The mixture is filtered, and the insoluble material is washed with a small amount of additional ethyl acetate. The combined filtrates are separated, and the aqueous layer is washed several times with fresh ethyl acetate. The combined organic layers are washed with 5% aqueous sodium carbonate solution and brine, then dried (sodium sulfate), and evaporated. The residue is purified by flash chromatography (1% methanol in dichloromethane elution) to give 1.4 g (26%) of product. A sample recrystallized from ethyl acetate-hexane had melting point (mp) 101–102° C.

Example 2

6-[2-(3-Phenoxy-propylamino)-ethoxy]-chromen-2-one hydrochloride

A mixture of 6-(2-bromo-ethoxy)-chromen-2-one (1.1 g, 4.1 mmol) and 3-phenoxy-1-propanamine, which can be synthesized in accordance with the procedure set forth by O. W. Lever, Jr., L. N. Bell, H. M. McGuire, and R. Ferone, *J. Med. Chem.*, 1985;28:1870, (1.2 g, 7.9 mmol) in 15 mL of toluene is stirred at reflux for 48 hours. The precipitated solid is filtered and washed with toluene. The combined filtrates are evaporated to an oil residue. Purification of the oil by flash chromatography (8% methanol in dichloromethane elution) gives 0.30 g (22%) of the product free base as an oil. The oil is dissolved in 15 mL of dichloromethane, and the solution is treated with hydrogen chloride gas. The precipitated hydrochloride salt is filtered, washed with ether, and recrystallized from acetonitrile to give 0.24 g of product, mp 180–182° C.

Similarly prepared by the procedures of Examples 1 and 2 are:

(a) (3-Phenoxy-propyl)-[2-quinolin-6-yloxy)-ethyl]-amine hydrochloride, mp 208–210° C.
(b) 8-[2-(3-Phenoxy-propylamino)-ethoxy]-chromen-2-one hydrochloride, mp 167–169° C.
(c) 7-[2-(3-Phenoxy-propylamino)-ethoxy]-chromen-2-one hydrochloride, mp 203–205° C.
(d) [2-(Dibenzofuran-2-yloxy)-ethyl]-(3-phenoxypropyl)-amine hydrochloride, mp 238–240° C.

Example 3

4-Methyl-7-[2-(3-phenoxy-propylamino)-ethoxy]-chromen-2-one Hydrochloride

A mixture of 7-(2-bromo-ethoxy)-4-methyl-chromem-2-one, which can be synthesized in accordance with the procedure set forth by D. B. Shinde and M. S. Shingare, *Asian J. Chem.*, 1994;6:265, (1.5 g, 5.3 mmol), 3-phenoxy-1-propanamine (0.72 g, 4.8 mmol), and potassium carbonate (0.72 g, 5.2 mmol) in 15 mL of N,N-dimethylformamide is heated at 90° C. for 16 hours. The cooled reaction mixture is filtered, and the filtrate is evaporated. The residue is dissolved in ether, and a small amount of methanol and the solution is treated with hydrogen chloride gas. The precipitated hydrochloride salt is filtered, washed with ether, and recrystallized from ethyl acetate-methanol to give 0.48 g (26%) of product, mp 195–196° C.

Similarly prepared by the procedures of Examples 1 and 3 are:

(a) 4-Methyl-6-[2-(3-phenoxy-propylamino)-ethoxy]-chromen-2-one hydrochloride, mp 205–206° C.
(b) [2-(Benzofuran-5-yloxy)-ethyl]-(3-phenoxy-propyl)-amine hydrochloride, mp 216–218° C.

Example 4

7-[(2-Phenylamino-ethylamino)-methyl]-chromen-2-one

A mixture of 7-bromomethyl-chromen-2-one, which can be synthesized in accordance with the procedure set forth by K. M. Jainamma and S. Sethna, *J. Indian Chem. Soc.*, 1973;50:790, (1.5 g, 6.3 mmol), N-phenylethylene-diamine (5.0 g, 37 mmol), and potassium carbonate (4.0 g, 29 mmol) in 200 mL of acetonitrile is stirred at reflux for 18 hours. The mixture is cooled and filtered, and the filtrate is evaporated. Purification of the residue by flash chromatography (10% 2-propanol in dichloromethane elution) followed by trituration of the product with ether gives 0.95 g (51%) of product, mp 91–92° C.

Similarly prepared by the procedure of Example 4 are:

(a) 7-{[2-(3-Chloro-4-hydroxymethyl-phenylamino)-ethylamino]-methyl}-chromen-2-one, mp 175–176° C.
(b) 7-{[2-(3,4-Dimethyl-phenylamino)-ethylamino]-methyl}-chromen-2-one, mp 92–95° C.
(c) 7-[(2-p-Tolylamino-ethylamino)-methyl]-chromen-2-one, mp 90° C.-dec
(d) 7-{[2-(3-Chloro-phenylamino)-ethylamino]-methyl}-chromen-2-one dihydrochloride, mp 273–275° C.
(e) 7-{[2-(4-Chloro-phenylamino)-ethylamino]-methyl}-chromen-2-one, mp 99–100° C.
(f) 7-{[2-(3-Chloro-4-methyl-phenylamino)-ethylamino]-methyl}-chromen-2-one, mp 77–78° C.
(g) 6-[(2-Phenylamino-ethylamino)-methyl]-chromen-2-one, mp 95–99° C.
(h) 6-{[2-(3-Chloro-4-methyl-phenylamino)-ethylamino]-methyl}-chromen-2-one hydrochloride, mp 200° C.-dec
(i) 7-[(3-Phenylamino-propylamino)-methyl]-chromen-2-one, mp 68–69° C.
(j) 6-[(2-Phenoxy-ethylamino)-methyl]-chromen-2-one hydrochloride, mp 196–198° C.
(k) 6-[(2-p-Tolyloxy-ethylamino)-methyl]-chromen-2-one, mp 72–72° C.
(l) 6-{[2-(4-Chloro-phenoxy)-ethylamino]-methyl}-chromen-2-one, mp 81–82° C.
(m) 7-[(2-Phenoxy-ethylamino)-methyl]-chromen-2-one, mp 62–64° C.
(n) 7-[(2-p-Tolyloxy-ethylamino)-methyl]-chromen-2-one, mp 90–91° C.
(o) 7-{[2-(4-Chloro-phenoxy)-ethylamino]-methyl}-chromen-2-one, mp 89–90° C.
(p) 7-[(2-Phenylsulfanyl-ethylamino)-methyl]-chromen-2-one hydrochloride, mp 279–280° C.
(q) 7-[(3-Phenyl-propylamino)-methyl]-chromen-2-one, mp 70–71° C.
(r) 7-{[3-(4-Chloro-phenoxy)-propylamino]-methyl}-chromen-2-one, mp 85–86° C.
(s) 7-[(3-p-Tolyloxy-propylamino)-methyl]-chromen-2-one, mp 91–93° C.
(t) 6-[(3-Phenoxy-propylamino)-methyl]-chromen-2-one, mp 81–83° C.

BIOLOGICAL METHODS

Cell Lines Expressing Dopamine Receptor Isoforms

A cell line expressing human dopamine D2 (Long form) receptors was purchased from Oregon Health Sciences University, Portland, Oreg. The D2 receptor cDNA was subcloned into an expression vector, pRc/CMV. The plasmids were transfected by electroporation into CHO K1 cells. A single stable transfectant, resistant to the antibiotic G418, was isolated and selected for use in the binding studies. For D4 binding, CHO K1 cells stably transfected to express the human recombinant dopamine D4.2 receptor subtype, as described by Shih, et al., "The expression and functional characterization of human dopamine D4.2 receptor in CHO K1 cells," *Soc. Neurosci.*, 1995;21 (Part 1):621 were used.

Cell Culture and Preparation of Cell Membranes

CHO K1 cells expressing either human D2 and D4.2 receptors were grown in 162 cm² culture flasks in F12 medium (Gibco Laboratories, Grand Island, N.Y.) supplemented with 10% fetal bovine serum (FBS, Hyclone, Logan, Utah) in an atmosphere of 5% $CO_2$/95% air at 37 EC. Cells were grown until confluent, after which growth medium was removed and replaced with 0.02% ethylene diamine tetracetate (EDTA) in a phosphate-buffered saline solution (Sigma Chemical Co., St. Louis, Mo.) and scraped from the flasks. The cells were centrifuged at about 1000×g for 10 minutes at 4° C. and then resuspended in TEM buffer (25 mM Tris-HCL, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20000×g at 4° C. for 20 minutes. Then the pellets were resuspended in appropriate buffer at 1 mL/flask and stored at −70° C. until used in the receptor binding assay.

Receptor Binding Assays: D2, D4.2 Dopamine Receptors

A cell membrane preparation (400 μL) was incubated in triplicate with 50 μL [³H]spiperone (0.2 nM for D2, 0.2 nM for D4.2), 50 μL buffer, or competing drugs where appropriate to give a final volume of 0.5 mL. After 60 minutes incubation at 25° C., the incubations were terminated by rapid filtration through Whatmann GF/B glass fibre filters (soaked for 1 hour in 0.5% polyethylenimine) on a cell harvester, with three washes of 1 mL ice-cold buffer. Individual filter disks containing the bound ligand were placed in counting vials with 4 mL of scintillation fluid (Ready Gel, Beckman Instrument, Inc., Fullerton, Calif.) and then counted in a Beckman LS-6800 liquid scintillation counter at an efficiency of 45%. Nonspecific binding was defined in presence of 1 mM of haloperidol.

Data Calculation

Saturation and competition binding data were analyzed using an iterative nonlinear least square curve-fitting Ligand program. In competition experiments, apparent $K_i$ values were calculated from $IC_{50}$ values by method of Cheng and Prusoff, "Relationship between the inhibition constant ($K_i$) and the concentration of inhibitor which causes 50% inhibition ($IC_{50}$) of an enzymatic reaction." *Biochem. Pharmacol.*, 1973;22:3099–3108. Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_d$ values were measured for the interaction of various ligands with the receptor. These were: [³H]spiperone binding, human D2, 0.116+0.01 and human D4.2, 0.093+ 0.005 nM (n=3). The test results are presented below.

| Example Number | D4, $K_i$ (nM) | D2, $K_i$ (nM) |
| --- | --- | --- |
| 2 | | |
| 2a | 12.8 | 578 |
| 2b | | |
| 2c | 1.6 | 249 |
| 2d | 78.7 | — |
| 3 | 1.9 | 231 |
| 3a | 70.2 | — |
| 3b | 1.2 | 502 |
| 4 | 5.8 | 2920 |
| 4a | 95 | — |
| 4b | 21 | — |
| 4c | 10 | 2087 |
| 4d | 42 | — |
| 4e | 14 | 696 |
| 4f | 16 | 5882 |
| 4g | 311 | — |
| 4h | | |
| 4i | 31 | — |
| 4j | 64 | — |
| 4k | 23.8 | 5882 |
| 4l | 13.5 | 4870 |
| 4m | 43 | — |
| 4n | 3.9 | 195 |
| 4o | 9.5 | 286 |
| 4p | 394 | — |
| 4q | 60 | — |
| 4r | 92 | — |
| 4s | 234 | — |
| 4t | 20 | 1066 |

We claim:

1. A compound having the Formula I

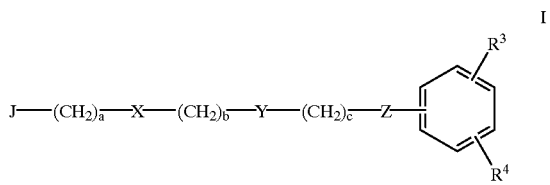

wherein

J is

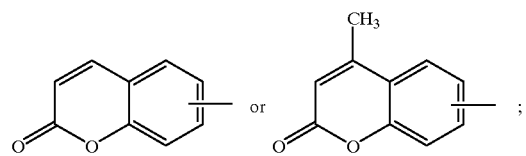

X is O, S, or NH;

Y is NH or a bond;

Z is O, S, NH, or a bond;

a, b and c are independently 0 to 3;

$R^1$ is hydrogen or R and $R^2$ taken together form a benzene ring;

$R^2$ is hydrogen; and $R^3$ and $R^4$ are independently hydrogen, hydroxyl, $C_1$–$C_6$ alkyl, $C_1$–$C_6$ alkoxy, halogen, nitro, phenyl, cyano, carboxy, carboxamido, carboalkoxy or hydroxymethyl, and the pharmaceutically acceptable salts, esters, amides, and prodrugs thereof.

2. A compound according to claim 1 wherein J is

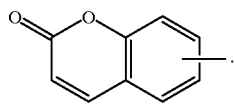

3. A compound according to claim 1 wherein J is

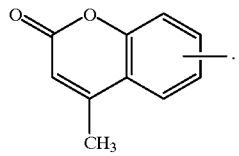

4. A compound according to claim 1 wherein a is 0, b is 2, c is 3, X is O, Y is NH, and Z is O.

5. A compound according to claim 1 wherein a is 1, X is NH, b is 2, Y is NH, c is 0, and Z is a bond.

6. A compound according to claim 1 wherein a is 1, X is NH, b is 2, Y is O, c is 0, and Z is a bond.

7. A compound according to claim 1 wherein $R^3$ and $R^4$ are independently hydrogen, $C_1$–$C_6$ alkyl, halogen, or hydroxymethyl.

8. A compound according to claim 1 wherein $R^3$ and $R^4$ are hydrogen.

9. A compound according to claim 1 that is a hydrohalide salt.

10. A compound according to claim 9 wherein the hydrohalide salt is a hydrochloride salt.

11. A compound of claim 1 that has the formula

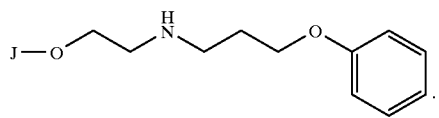

12. A compound of claim 1 that has the formula

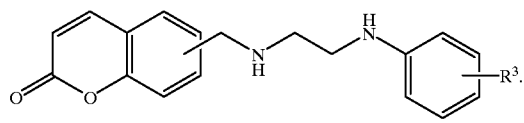

13. A pharmaceutically acceptable composition that comprises a compound of claim 1.

14. A method of treating psychosis, the method comprising administering to a patient having psychosis a therapeutically effective amount of a compound of claim 1.

15. A method of treating schizophrenia, the method comprising administering to a patient having schizophrenia therapeutically effective amount of a compound of claim 1.

16. The compounds:

6-[2-(3-Phenoxy-propylamino)-ethoxy]-chromen-2-one hydrochloride;
8-[2-(3-Phenoxy-propylamino)-ethoxy]-chromen-2-one hydrochloride;
7-[2-(3-Phenoxy-propylamino)-ethoxy]-chromen-2-one hydrochloride;
4-Methyl-7-[2-(3-phenoxy-propylamino)-ethoxy]-chromen-2-one hydrochloride;
4-Methyl-6-[2-(3-phenoxy-propylamino)-ethoxy]-chromen-2-one hydrochloride;
7-[(2-Phenylamino-ethylamino)-methyl]-chromen-2-one;
7-{[2-(3-Chloro-4-hydroxymethyl-phenylamino)-ethylamino]-methyl}-chromen-2-one;
7-{[2-(3,4-Dimethyl-phenylamino)-ethylamino]-methyl}-chromen-2-one;
7-[(2-p-Tolylamino-ethylamino)-methyl]-chromen-2-one;
7-{[2-(3-Chloro-phenylamino)-ethylamino]-methyl}-chromen-2-one dihydrochloride;
7-{[2-(4-Chloro-phenylamino)-ethylamino]-methyl)}-chromen-2-one;
7-{[2-(3-Chloro-4-methyl-phenylamino)-ethylamino]-methyl}-chromen-2-one;
6-[(2-Phenylamino-ethylamino)-methyl]-chromen-2-one;
6-{[2-(3-Chloro-4-methyl-phenylamino)-ethylamino]-methyl}-chromen-2-one hydrochloride;
7-[(3-Phenylamino-propylamino)-methyl]-chromen-2-one;
6-[(2-Phenoxy-ethylamino)-methyl]-chromen-2-one hydrochloride;
6-[(2-p-Tolyloxy-ethylamino)-methyl]-chromen-2-one;
6-{[2-(4-Chloro-phenoxy)-ethylamino]-methyl}-chromen-2-one;
7-[(2-Phenoxy-ethylamino)-methyl]-chromen-2-one;
7-[(2-p-Tolyloxy-ethylamino)-methyl]-chromen-2-one;
7-{[2-(4-Chloro-phenoxy)-ethylamino]-methyl}-chromen-2-one;
7-[(2-Phenylsulfanyl-ethylamino)-methyl]-chromen-2-one hydrochloride;
7-[(3-Phenyl-propylamino)-methyl]-chromen-2-one;
7-{[3-(4-Chloro-phenoxy)-propylamino]-methyl}-chromen-2-one;
7-[(3-p-Tolyloxy-propylamino)-methyl]-chromen-2-one; or
6-[(3-Phenoxy-propylamino)-methyl]-chromen-2-one.

* * * * *